(12) United States Patent
Ohta et al.

(10) Patent No.: US 8,406,492 B2
(45) Date of Patent: Mar. 26, 2013

(54) IMAGE DETECTING SYSTEM, IMAGE DETECTING METHOD AND COMPUTER READABLE MEDIUM

(75) Inventors: Yasunori Ohta, Kanagawa (JP); Kazuharu Ueda, Tokyo (JP); Tatsuya Aoyama, Kanagawa (JP); Akira Yoda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 931 days.

(21) Appl. No.: 12/123,012

(22) Filed: May 19, 2008

(65) Prior Publication Data

US 2008/0287784 A1      Nov. 20, 2008

(30) Foreign Application Priority Data

May 18, 2007   (JP) .................................. 2007-132682

(51) Int. Cl.
*G06K 9/00* (2006.01)
(52) U.S. Cl. ........................................ 382/128; 600/504
(58) Field of Classification Search .................. 378/98.9, 378/51, 62, 143, 98.12, 98.11, 8; 600/440, 600/438, 458, 443, 437; 382/128
See application file for complete search history.

(56) References Cited

U.S. PATENT DOCUMENTS

| | | | | |
|---|---|---|---|---|
| 6,409,671 B1 * | 6/2002 | Eriksen et al. | ................ | 600/458 |
| 2001/0038682 A1 * | 11/2001 | Salb | ............................ | 378/98.9 |
| 2003/0114759 A1 * | 6/2003 | Skyba et al. | .................. | 600/458 |
| 2009/0124907 A1 * | 5/2009 | Bruce et al. | ................... | 600/458 |

FOREIGN PATENT DOCUMENTS

| | | |
|---|---|---|
| JP | 2003-190148 A | 7/2003 |
| JP | 2005-95340 A | 4/2005 |

OTHER PUBLICATIONS

Office Action, dated Dec. 6, 2011, issued in corresponding JP Application No. 2007-132682, 3 pages in English and Japanese.

* cited by examiner

*Primary Examiner* — Elmer Chao
(74) *Attorney, Agent, or Firm* — Sughrue Mion, PLLC

(57) ABSTRACT

There is provided an image detecting system including an image detecting section that detects a moving image of an examination subject into which a radiopaque contrast medium flows through one of an artery and a portal vein, and a change image generating section that generates a change image representing a change in the moving image. Here, the change is caused by movement of the radiopaque contrast medium after a timing at which the radiopaque contrast medium that has flown into one of the artery and the portal vein flows into capillaries.

17 Claims, 5 Drawing Sheets

IMAGE DETECTING SYSTEM, IMAGE DETECTING METHOD AND COMPUTER READABLE MEDIUM

CROSS REFERENCE TO RELATED APPLICATION

The present application claims priority from a Japanese Patent Application No. 2007-132682 filed on May 18, 2007, the contents of which are incorporated herein by reference.

BACKGROUND

1. Technical Field

The present invention relates to an image detecting system, an image detecting method and a computer readable medium. More particularly, the present invention relates to a radiation image detecting system and a radiation image detecting method for detecting an image by using radiation, and to a computer readable medium for use with the radiation image detecting system.

2. Related Art

A known blood flow analysis apparatus calculates a ratio or difference between a parameter indicating hemodynamics unique to a tissue of an examination subject and a parameter indicating hemodynamics unique to a desired reference region, where the parameters indicate the hemodynamics based only on the time density curves of the tissue and the reference region, and visually presents the result of the calculation, as disclosed in Japanese Patent Application Publication No. 2005-95340, for example. Also, another known blood flow analysis apparatus computes an index relating to local hemodynamics, as disclosed in Japanese Patent Application Publication No. 2003-190148, for example. This blood flow analysis apparatus obtains a first time density curve relating to an artery in a specified site of an examination subject and a second time density curve relating to a tissue in the specified site, from a plurality of successive images relating to the specified site, where the examination subject is injected with a radiopaque contrast medium. The blood flow analysis apparatus then calculates a transfer function representing local hemodynamics of a tissue for each artery by using the curve-fitting technique, in such a manner that the residual of the second time density curve with respect to the convolution result of the transfer function and the first time density curve takes a minimum value. The blood flow analysis apparatus subsequently calculates an index relating to the local hemodynamics for each artery, from the transfer function. The blood flow analysis apparatus then creates index maps corresponding to the arteries, and combines the index maps into a single map, according to the residual with respect to each first time density curve.

The techniques disclosed in the above-mentioned publications No. 2005-95340 and No. 2003-190148 can analyze the blood flow in a blood vessel. These techniques, however, cannot reveal how blood is supplied to a tissue. For this drawback, the above-described techniques cannot easily identify a tissue that is fed by blood, for example, a tumor.

SUMMARY

Therefore, it is an object of an aspect of the innovations herein to provide an image detecting system, an image detecting method and a computer readable medium which are capable of overcoming the above drawbacks accompanying the related art. The above and other objects can be achieved by combinations described in the independent claims. The dependent claims define further advantageous and exemplary combinations of the innovations herein.

According to the first aspect related to the innovations herein, one exemplary image detecting system may include an image detecting system including an image detecting section that detects a moving image of an examination subject into which a radiopaque contrast medium flows through one of an artery and a portal vein, and a change image generating section that generates a change image representing a change in the moving image. Here, the change is caused by movement of the radiopaque contrast medium after a timing at which the radiopaque contrast medium that has flown into one of the artery and the portal vein flows into capillaries.

According to the second aspect related to the innovations herein, one exemplary image detecting method may include an image detecting method including detecting a moving image of an examination subject into which a radiopaque contrast medium flows through one of an artery and a portal vein, and generating a change image representing a change in the moving image. Here, the change is caused by movement of the radiopaque contrast medium after a timing at which the radiopaque contrast medium that has flown into one of the artery and the portal vein flows into capillaries.

According to the third aspect related to the innovations herein, one exemplary computer readable medium may include a computer readable medium storing thereon a program for use with an image detecting system. When executed, the program causes a computer to function as an image detecting section that detects a moving image of an examination subject into which a radiopaque contrast medium flows through one of an artery and a portal vein, and a change image generating section that generates a change image representing a change in the moving image. Here, the change is caused by movement of the radiopaque contrast medium after a timing at which the radiopaque contrast medium that has flown into one of the artery and the portal vein flows into capillaries.

The summary clause does not necessarily describe all necessary features of the embodiments of the present invention. The present invention may also be a sub-combination of the features described above. The above and other features and advantages of the present invention will become more apparent from the following description of the embodiments taken in conjunction with the accompanying drawings.

DESCRIPTION OF EXEMPLARY EMBODIMENTS

Some aspects of the invention will now be described based on an embodiment, which does not intend to limit the scope of the present invention, but exemplifies the invention. All of the features and the combinations thereof described in the embodiment are not necessarily essential to the invention.

Figure 1:
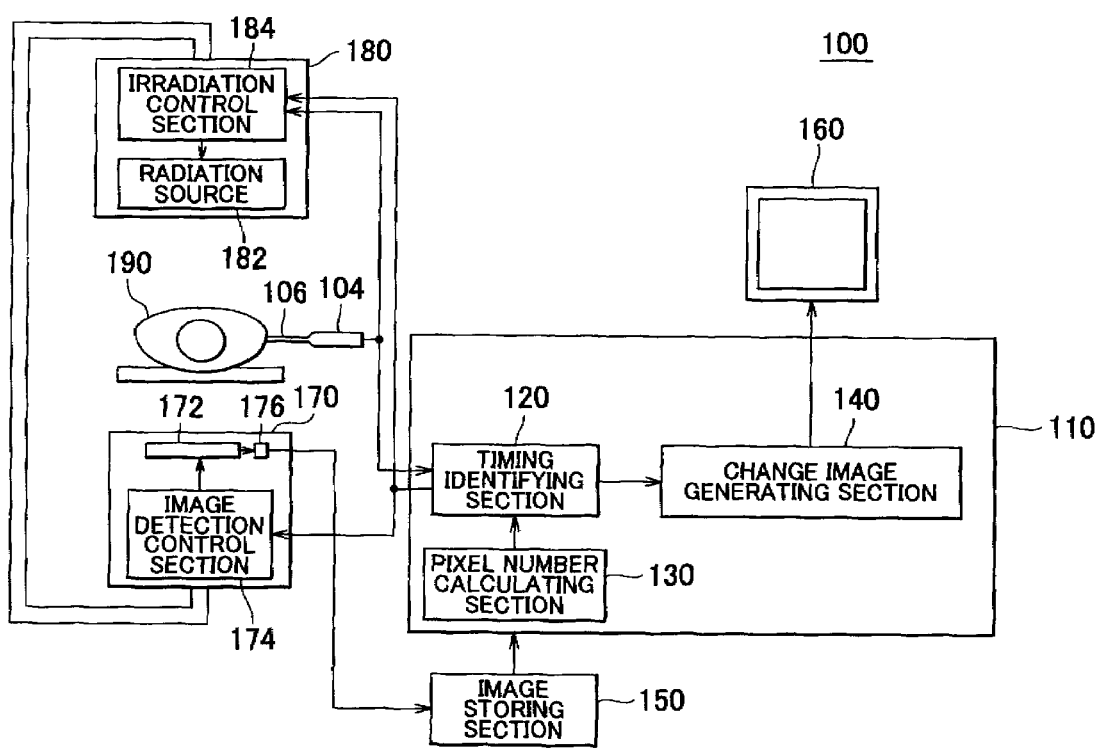
FIG. 1 illustrates an example of a radiation image detecting system 100, together with an examination subject 190.

FIG. 1 illustrates an example of a radiation image detecting system 100 relating to an embodiment of the present invention, together with an examination subject 190. The radiation image detecting system 100 detects a change image of the examination subject 190 into which a radiopaque contrast medium has been injected, by using radiation. The radiation image detecting system 100 includes an image processing apparatus 110, an image storing section 150, a display section 160, a radiation image detecting section 170, a radiation generating section 180, a radiopaque contrast medium injector 104, and a catheter 106. The radiation generating section 180 generates radiation to be irradiated to the examination subject 190.

The image processing apparatus 110 includes a timing identifying section 120, a pixel number calculating section 130, and a change image generating section 140. The radiation image detecting section 170 includes a radiation detecting section 172, a radiation image generating section 176, and an image detection control section 174. The radiation generating section 180 includes a radiation source 182 and an irradiation control section 184.

The radiopaque contrast medium injector 104 injects a radiopaque contrast medium into the catheter 106. The catheter 106 is inserted into the examination subject 190 so as to inject the radiopaque contrast medium from the radiopaque contrast medium injector 104 into the body of the examination subject 190. Specifically speaking, the catheter 106 is inserted into a blood vessel of the examination subject 190, so as to inject the radiopaque contrast medium into the blood vessel of the examination subject 190. Here, the blood vessel includes an artery and a portal vein. To be more specific, the blood vessel includes a hepatic artery and a hepatic portal vein.

The radiation source 182 generates radiation to be irradiated to the examination subject 190, under the control of the irradiation control section 184. For example, the irradiation control section 184 controls the radiation source 182 to generate radiation to be irradiated to the examination subject 190, when detecting that the radiopaque contrast medium injector 104 injects the radiopaque contrast medium into the catheter 106. The irradiation control section 184 may detect whether the radiopaque contrast medium injector 104 injects the radiopaque contrast medium into the catheter 106, with reference to a change in the pressure of the radiopaque contrast medium injected from the radiopaque contrast medium injector 104 into the catheter 106.

The irradiation control section 184 may control the radiation source 182 to generate radiation to be irradiated to the examination subject 190 at a timing when a predetermined time duration has elapsed since the irradiation control section 184 detects that the radiopaque contrast medium injector 104 injects the radiopaque contrast medium into the catheter 106. The predetermined time duration may be equal to a time duration from when the radiopaque contrast medium injector 104 starts injecting the radiopaque contrast medium into the catheter 106 to when the radiopaque contrast medium starts flowing out from the end of the catheter 106 which is inserted into the examination subject 190. Here, generating the radiation to be irradiated to the examination subject 190 includes opening the diaphragm to partially block the radiation generated by the radiation source 182 and irradiating the remaining radiation to the examination subject 190.

The radiation image detecting section 170 detects a radiation moving image of the examination subject 190 whose artery or portal vein is injected with the radiopaque contrast medium. Specifically speaking, the radiation detecting section 172 detects radiation that has been generated by the radiation source 182 and has passed through the examination subject 190. The image detection control section 174 controls the time period for which the radiation detecting section 172 detects the radiation. Specifically speaking, the image detection control section 174 controls the timing at which the radiation detecting section 172 starts detecting the radiation and the time duration for which the radiation detecting section 172 continues detecting the radiation. The radiation detecting section 172 continues detecting the radiation for each time period determined by the image detection control section 174.

The radiation image generating section 176 generates a radiation image with reference to the amount of the radiation detected by the radiation detecting section 172. Specifically speaking, the radiation image generating section 176 generates a radiation image corresponding to each time period for which the radiation detecting section 172 detects the radiation, with reference to the amount of the radiation detected by the radiation detecting section 172. Therefore, the radiation moving image includes a plurality of radiation images. The radiation image generating section 176 supplies the generated radiation images to the image storing section 150. The image storing section 150 stores the radiation images supplied from the radiation image generating section 176. Here, the image storing section 150 may be a volatile memory.

The image processing apparatus 110 performs image processing on the radiation moving image detected by the radiation image detecting section 170, and supplies the resulting radiation moving image to the display section 160. Specifically speaking, the timing identifying section 120 identifies the timing at which the radiopaque contrast medium that has been injected into the artery or portal vein flows into capillaries, with reference to what is shown by the radiation moving image. The change image generating section 140 generates a change image indicating the amount of a change in the radiation moving image which is caused by the movement of the radiopaque contrast medium after the timing identified by the timing identifying section 120.

Specifically speaking, the pixel number calculating section 130 calculates the number of pixels whose pixel values fall within a predetermined range in each of the radiation images constituting the radiation moving image. The timing identifying section 120 may identify, as the timing at which the radiopaque contrast medium flows into the capillaries, the timing at which the number of pixels calculated by the pixel number calculating section 130 becomes equal to or smaller than a predetermined number after taking a local maximal values.

The change image generating section 140 supplies the generated change image to the display section 160. The display section 160 displays the change image that has been supplied from the change image generating section 140. The change image generating section 140 may generate a change image that is colored according to the amount of the change in the radiation moving image which is caused after the timing identified by the timing identifying section 120.

The change image generating section 140 may generate a change image when the radiopaque contrast medium is injected into the artery of the examination subjection 190 and a change image when the radiopaque contrast medium is injected into the portal vein of the examination subject 190. For example, the change image generating section 140 may generate a change image when the radiopaque contrast medium is injected into the hepatic artery of an examined person and a change image when the radiopaque contrast medium is injected into the hepatic portal vein of the examined person. The display section 160 may emphasize the difference between these change images generated by the change image generating section 140 when displaying the images. For example, the display section 160 may display a differential image between the change images generated by the change image generating section 140.

The radiation detecting section 172 may be a solid-state radiation detector such as a FPD. In the present embodiment, the radiation may be an electromagnetic radiation such as an X ray and a γ ray, or a particle beam such as an alpha ray. The examination subject 190 may be a human or animal. The radiation image detecting system 100 may be a radiation tomographic system such as an X-ray CT system.

Figure 2:
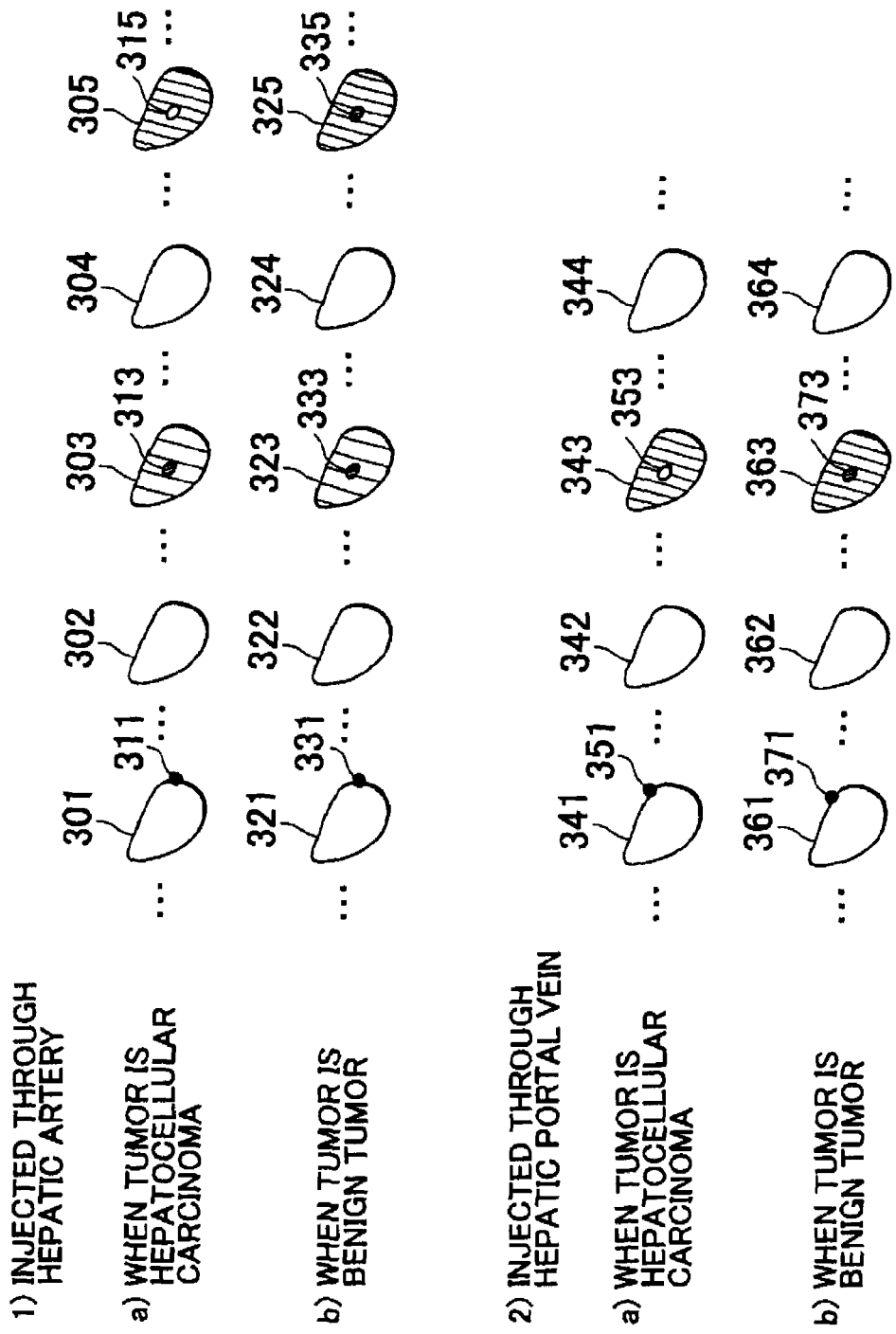
FIG. 2 schematically illustrates the transition of the cross-sectional image of a liver which is observed when a radiopaque contrast medium is injected into the liver via a hepatic artery and the transition of the cross-sectional image of the liver which is observed when the radiopaque contrast medium is injected into the liver via the hepatic portal vein.

FIG. 2 schematically illustrates the transition of the cross-sectional image of a liver which is observed when the radiopaque contrast medium is injected into the liver via the hepatic artery and the transition of the cross-sectional image of the liver which is observed when the radiopaque contrast medium is injected into the liver via the hepatic portal vein. The following first explains the transition of the cross-sectional image of the liver which is observed when the radiopaque contrast medium is injected into the liver via the hepatic artery. Here, the following explanation is made with an assumption that the liver has a tumor. The following explanation also describes the difference in the images between when the tumor is a hepatocellular carcinoma and when the tumor is a benign tumor.

When the radiopaque contrast medium is injected through a proper or common hepatic artery, hepatic artery regions 311 and 331 are highlighted with the radiopaque contrast medium (see images 301 and 321). Subsequently, since the radiopaque contrast medium flows into the capillaries, no regions are highlighted with the radiopaque contrast medium (see images 302 and 322). After this, while the liver parenchyma is weakly highlighted by the radiopaque contrast medium in a gradual manner, tumor regions 313 and 333 are strongly highlighted by the radiopaque contrast medium (see images 303 and 323). Following this, the radiopaque contrast medium flows out of the liver as the time elapses. Therefore, the image of the radiopaque contrast medium gradually disappears (see images 304 and 324).

As the time further elapses, the radiopaque contrast medium reaches the portal vein system via the greater circulation and flows into the liver through the portal vein system. As a result, the liver parenchyma is strongly highlighted (images 305 and 325). Since the liver is fed by the artery less than by the portal vein, the liver parenchyma is highlighted more strongly in the images 305 and 325 than in the images 303 and 323. Here, while a hepatocellular carcinoma is not fed by the hepatic portal vein, except for an early hepatocellular carcinoma, a benign tumor is fed by both the hepatic artery and the hepatic portal vein. For the reasons stated above, at this stage, the tumor region 315 is not highlighted since the tumor is a hepatocellular carcinoma, but the tumor region 335 is strongly highlighted since the tumor is a benign tumor.

The following explains the transition of the cross-sectional image of the liver which is observed when the radiopaque contrast medium is injected into the liver via the hepatic portal vein. When injected via a superior mesenteric artery, the radiopaque contrast medium reaches the portal vein system so that portal vein regions 351 and 371 are highlighted (see images 341 and 361). Subsequently, since the radiopaque contrast medium flows into the capillaries, no regions are highlighted with the radiopaque contrast medium (see images 342 and 362). After this, the radiopaque contrast medium gradually penetrates the liver. For the reasons stated above, the liver parenchyma is more strongly highlighted than when the same quantity of the radiopaque contrast medium is injected via the hepatic artery (see images 343 and 363). At this stage, the tumor region 353 is not highlighted since the tumor is a hepatocellular carcinoma but the tumor region 373 is strongly highlighted since the tumor is a benign tumor, similarly to the above. After this, the radiopaque contrast medium flows out of the liver, so that the image of the liver gradually disappears (see images 344 and 364).

As described in the above, when the tumor is a hepatocellular carcinoma, the image 303 obtained by the radiopaque contrast medium flowing into the liver through the hepatic artery differs from the images 343 that is obtained by the radiopaque contrast medium flowing into the liver through the hepatic portal vein or the image 305, in terms of the manner in which the tumor region is highlighted. The image processing apparatus 110 generates the change image in which the above difference stands out, and causes the display section 160 to display the generated change image.

Figure 3:
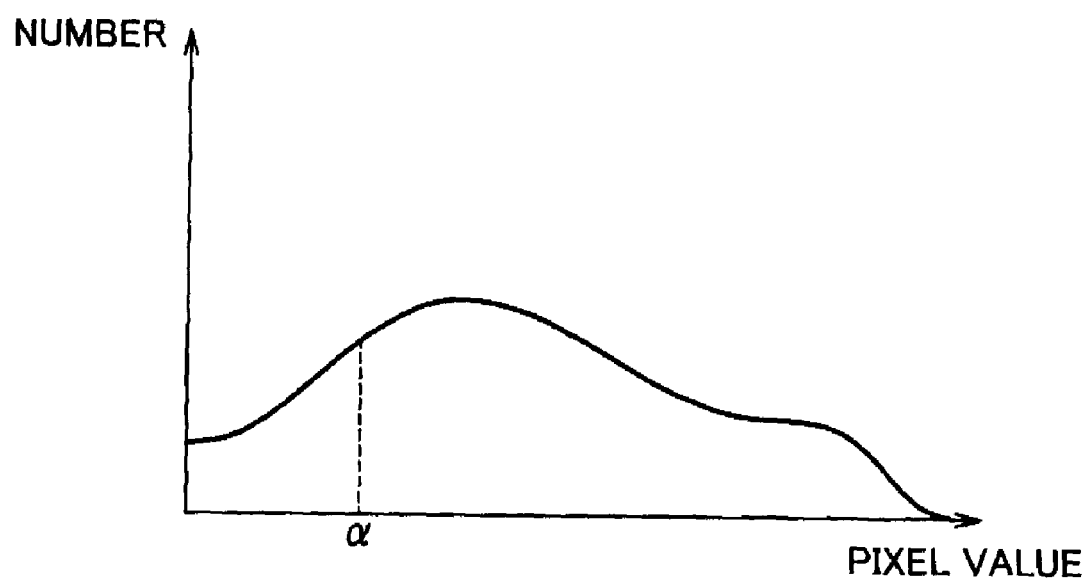
FIG. 3 is an exemplary histogram of a radiation image.

FIG. 3 is an exemplary histogram of the radiation image generated by the radiation image generating section 176. Here, it is assumed that, as the amount of the radiation detected by the radiation detecting section 172 decreases, the pixel values of the radiation image generated by the radiation image generating section 176 relating to the present embodiment decrease. The histogram of FIG. 3 is a histogram of a radiation image. The pixel value ∝ is the upper limit value of the range of the pixel values within which the pixel number calculating section 130 can count the number of pixels. Which is to say, the pixel number calculating section 130 counts the number of pixels, in each of the radiation images, whose pixel values are equal to or smaller than the pixel value ∝. In other words, the pixel number calculating section 130 calculates the number of pixels whose pixel values fall within the range from 0 to ∝.

Figure 4:
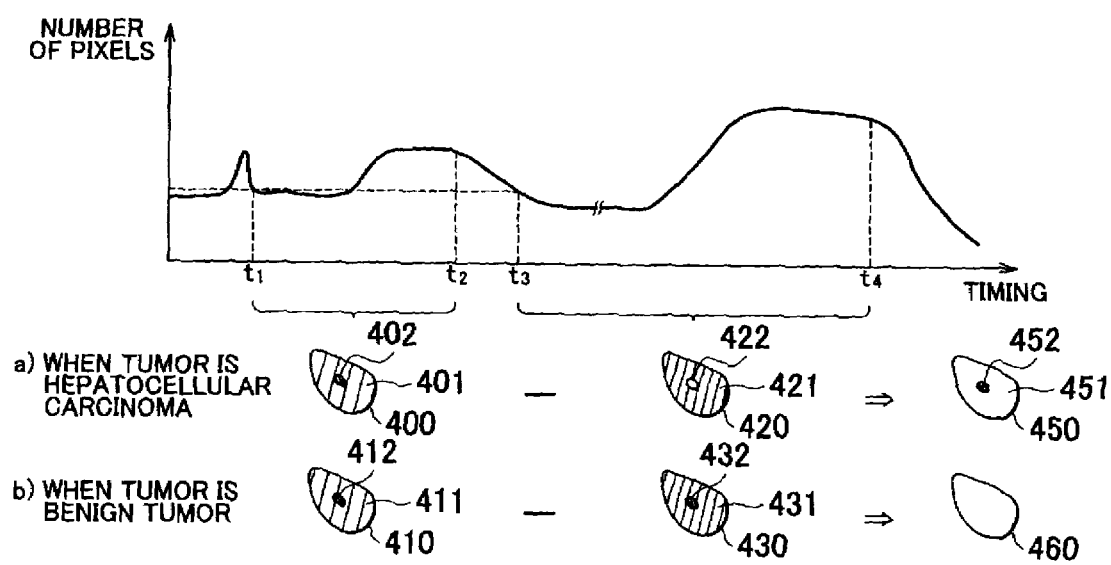
FIG. 4 illustrates the variation, over time, of the number of pixels (N) which is counted by a pixel number calculating section 130, together with change images which are generated by a change image generating section 140, as an example.

FIG. 4 illustrates the variation, over time, of the number of pixels (N) which is counted by the pixel number calculating section 130, together with the change images generated by the change image generating section 140, as an example. In the graph shown in FIG. 4, the vertical axis represents the number of pixels (N) and the horizontal axis represents the time. The exemplary variation, over time, of the number of pixels (N) illustrated in FIG. 4 is observed when the radiopaque contrast medium is injected into the liver through the hepatic artery. When a certain time elapses after the radiopaque contrast medium is injected, the artery region is highlighted with the radiopaque contrast medium. Therefore, the pixels whose pixel values are lower than the pixel value ∝ increase, and the number of pixels (N) peaks. Subsequently, since the radiopaque contrast medium flows into the capillaries, the number of pixels (N) drops to the level that is substantially the same as the level before the peak.

The timing identifying section 120 identifies, as the timing at which the radiopaque contrast medium flows into the capillaries, a timing t1 at which the number of pixels (N) falls below a predetermined first reference pixel number after peaking. The change image generating section 140 starts integrating the pixel values of the radiation images, from the timing t1 identified by the timing identifying section 120. Specifically speaking, the change image generating section 140 adds together, for each pixel, the pixel values of the radiation images supplied from the image storing section 150. The change image generating section 140 continues adding together the pixel values from the timing t1 to a timing t2 during a predetermined time duration.

After the timing t1, the liver parenchyma is gradually highlighted. The radiopaque contrast medium remains in the liver for a predetermined time period. Subsequently, the radiopaque contrast medium gradually flows out of the liver. Therefore, the number of pixels (N) decreases, and finally falls below the first reference pixel number at a timing t3.

The change image generating section 140 may continue integrating the pixel values from the timing t1 to the timing t3, or from the timing t1 to a timing at which the number of pixels N falls below a predetermined second reference pixel number that is larger than the first reference pixel number.

By integrating the pixel values in the above-stated manner, the change image generating section 140 generates the change image. A change image 400 is an example of the change image generated when the tumor is a hepatocellular carcinoma, and a change image 410 is an example of the change image generated when the tumor is a benign tumor. The pixels of liver parenchyma 401 and 411 and tumor regions 402 and 412 have lower pixel values when the radiopaque contrast medium is injected than when the radiopaque contrast medium is not injected. Here, the change image generating section 140 can enhance the difference in pixel value by adding together the pixel values. Furthermore, by adding together the pixel values, the change image generating section 140 can increase the difference in pixel value between the tumor regions 402 and 412 and the liver parenchyma 401 and 411. Therefore, the present embodiment can prevent such a failure that the tumor region is concealed by noise and thus difficult to be observed. As a result, the change image generating section 140 can generate the change images 400 and 410 in which the tumor regions 402 and 412 stand out.

The change image generating section 140 resumes adding together the pixel values from the timing t3. After the timing t3, the number of pixels (N) increases again since the radiopaque contrast medium starts flowing into the liver through the portal vein system via the greater circulation, stays at a high level for a predetermined time period, and then starts decreasing. Therefore, the change image generating section 140 continues adding together the pixel values, from the timing t3 to a timing t4 for a predetermined time duration that is longer than a time duration required by the radiopaque contrast medium to flow into the liver via the portal vein system after running through the greater circulation.

By integrating the pixel values from the timing t3 to the timing t4, the change image generating section 140 generates the change image. A change image 420 is an example of the change image generated when the tumor is a hepatocellular carcinoma, and a change image 430 is an example of the change image generated when the tumor is a benign tumor. When the tumor is a hepatocellular carcinoma, the tumor region 422 stands out by having higher pixel values than the liver parenchyma 421. When the tumor is a benign tumor, the tumor region 432 stands out by having lower pixel values than the liver parenchyma 431. In this way, the change image generating section 140 can generate the change images 420 and 430 in which the tumor regions 422 and 432 stand out.

As described in the above, the change image generating section 140 generates the change image which is represented by values obtained by integrating the pixel values of the radiation moving image during the predetermined time period after the timing identified by the timing identifying section 120. The change image generating section 140 generates the change image which is represented by values obtained by integrating, for the predetermined time period, the difference in pixel values between the radiation moving image detected after the timing identified by the timing identifying section 120 and a radiation image detected by the radiation image detecting section 170 at a timing near the timing identified by the timing identifying section 120.

To make the tumor region more distinguishable, the change image generating section 140 may generate a differential image between the change images 420 and 400, or a differential image between the change images 430 and 410. For example, the change image generating section 140 may adjust the luminance of at least one of the images 420 and 400 such that the pixel values of the liver parenchyma 401 indicate substantially the same luminance level as the pixel values of the liver parenchyma 421, then generate a differential image 450 by calculating a difference between the resulting images 400 and 420, and supply the generated differential image 450 to the display section 160. In this manner, the radiation image detecting system 100 can acquire the image in which the tumor region 452 stands out more. When the tumor is a benign tumor, the above-described procedure produces a differential image 460 in which the liver region is essentially canceled out. Which is to say, the image generated by the change image generating section 140 when the tumor is a hepatocellular carcinoma shows the tumor region clearly differently from the image generated when the tumor is a benign tumor.

In the above exemplary case, the change image generating section 140 generates the differential image 450 between the change images 400 and 420, and causes the display section 160 to display the image in which the tumor region stands out. As an alternative example, the change image generating section 140 may generate a first image by coloring each pixel of the image 400 with a first color having an intensity determined in accordance with the pixel value of the pixel, and a second image by coloring each pixel of the image 420 with a second color having an intensity determined in accordance with the pixel value of the pixel. Here, the change image generating section 140 first adjusts the luminance level of the liver parenchyma 401 in the image 400 and the luminance level of the liver parenchyma 421 in the image 420 so as to be substantially the same, and then colors the images 400 and 420 respectively with the first and second colors. Subsequently, the change image generating section 140 aligns the tumor regions 402 and 422 with each other and overlaps the first and second images, thereby generating an overlap image.

In this case, the liver parenchyma region of the overlap image has a color with color components of the first and second colors, and the color components have substantially the same luminance level. The tumor region of the overlap image similarly has a color with the color components of the first and second colors, but the color component of the first color has a low luminance level and the color component of the second color has a high luminance level. Which is to say, the change image generating section 140 can generate the overlap image in which the tumor region stands out due to its color when the tumor region is a hepatocellular carcinoma. Therefore, the display section 160 enables a person to easily notice the difference between the liver parenchyma and the tumor region. As described above, the display section 160 overlaps an image obtained by coloring, with the first color, a change image generated by the change image generating section 140 when the radiopaque contrast medium is injected into the artery of the examination subject and an image obtained by coloring, with the second color, a change image generated by the change image generating section 140 when the radiopaque contrast medium is injected into the portal vein of the examination subject, when displaying these images.

When the tumor is a benign tumor, the above-described coloring procedure produces an overlap image in which the entire liver has a color with color components of the first and second colors which have substantially the same luminance level. Therefore, the overlap image generated when the tumor is a hepatocellular carcinoma can be clearly different from the overlap image generated when the tumor is a benign tumor. By selecting a color easily noticeable by human eyes for the second color, the radiation image detecting system 100 can make the tumor region more distinguishable when the tumor is a hepatocellular carcinoma.

According to the above description, the change image generating section 140 generates the change image by simply adding together the pixel values of the radiation images. Alternatively, the change image generating section 140 may integrate the pixel values of the differential images between the radiation images and a reference image. This method can make the change caused by the radiopaque contrast medium more distinguishable. Here, the reference image may be an image obtained before the radiopaque contrast medium is injected into the liver. For example, the reference image may be a radiation image detected at the timing t1. In this way, the change image generating section 140 generates the change image which is represented by the values obtained by integrating, during a predetermined time period, the difference in pixel value between the radiation moving image detected after the timing identified by the timing identifying section 120 and a radiation image of the examination subject which is detected when the radiopaque contrast medium is not injected.

According to the above description, the radiopaque contrast medium is injected through the proper or common hepatic artery, and the change image generating section 140 generates a change image at the timing when the radiopaque contrast medium flows into the liver through the hepatic artery and generates a change image at the timing when the radiopaque contrast medium afterwards flows again into the liver through the portal vein system. As described above with reference to FIG. 2, however, the change image generating section 140 can generate change images having the same characteristics as the images 420 and 430 by using substantially the same method as the method used when the radiopaque contrast medium is injected through the proper or common hepatic artery, even when the radiopaque contrast medium is injected through the superior mesenteric artery and flows into the liver through the portal vein.

The above section describes, as an example, the operations performed by the radiation image detecting system 100 to detect images of a liver. By performing the same image processing, however, the radiation image detecting system 100 can also be used to observe how blood is supplied from a blood vessel to a different tissue of the examination subject 190 than the liver.

Figure 5:
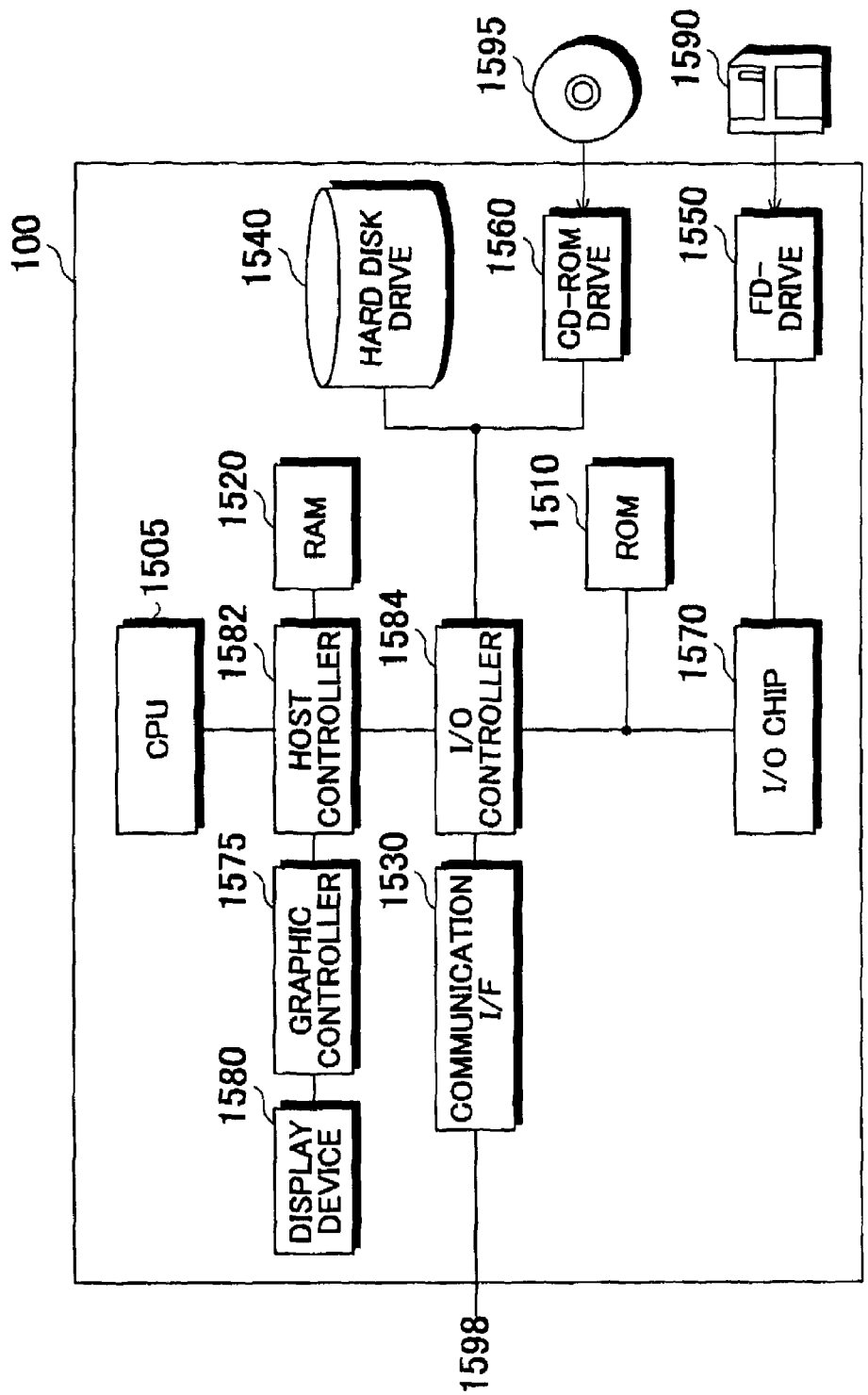
FIG. 5 illustrates an exemplary hardware configuration of the radiation image detecting system 100.

FIG. 5 illustrates an exemplary hardware configuration of the radiation image detecting system 100. The radiation image detecting system 100 is constituted by a CPU surrounding section, an input/output (I/O) section and a legacy I/O section. The CPU surrounding section includes a CPU 1505, a RAM 1520, a graphic controller 1575, and a display device 1580 which are connected to each other by means of a host controller 1582. The I/O section includes a communication interface 1530, a hard disk drive 1540, and a CD-ROM drive 1560 which are connected to the host controller 1582 by means of an I/O controller 1584. The legacy I/O section includes a ROM 1510, a flexible disk drive 1550, and an I/O chip 1570 which are connected to the I/O controller 1584.

The host controller 1582 connects the RAM 1520 with the CPU 1505 and graphic controller 1575 which access the RAM 1520 at a high transfer rate. The CPU 1505 operates in accordance with programs stored on the ROM 1510 and RAM 1520, to control the constituents. The graphic controller 1575 obtains image data which is generated by the CPU 1505 or the like on a frame buffer provided within the RAM 1520, and causes the display device 1580 to display the obtained image data. Alternatively, the graphic controller 1575 may include therein a frame buffer for storing thereon image data generated by the CPU 1505 or the like.

The I/O controller 1584 connects, to the host controller 1582, the hard disk drive 1540, communication interface 1530 and CD-ROM drive 1560 which are I/O devices operating at a relatively high rate. The hard disk drive 1540 stores thereon programs and data to be used by the CPU 1505. The communication interface 1530 couples to the network communication apparatus 1598, to transmit/receive programs or data. The CD-ROM drive 1560 reads programs or data from a CD-ROM 1595, and supplies the read programs or data to the hard disk drive 1540 and communication interface 1530 via the RAM 1520.

The I/O controller 1584 is also connected to the ROM 1510, flexible disk drive 1550 and I/O chip 1570 which are I/O devices operating at a relatively low rate. The ROM 1510 stores thereon a boot program executed by the radiation image detecting system 100 at the start up, programs dependent on the hardware of the radiation image detecting system 100, and the like. The flexible disk drive 1550 reads programs or data from a flexible disk 1590, and supplies the read programs or data to the hard disk drive 1540 and communication interface 1530 via the RAM 1520. The I/O chip 1570 is used to connect a variety of I/O devices such as the flexible disk drive 1550 via, for example, a parallel port, a serial port, a keyboard port, a mouse port or the like.

The program to be executed by the CPU 1505 is provided by a user in the state of being stored on a recording medium such as the flexible disk 1590, the CD-ROM 1595, and an IC card. The program may be stored on the recording medium in the state of being compressed or not being compressed. The program is installed from the recording medium onto the hard disk drive 1540, read by the RAM 1520, and executed by the CPU 1505.

The program executed by the CPU 1505 causes the radiation image detecting system 100 to function as the image processing apparatus 110, image storing section 150, display section 160, radiation image detecting section 170, and radiation generating section 180, described with reference to FIGS. 1 to 4. In addition, the program causes the image processing apparatus 110 to function as the timing identifying section 120, pixel number calculating section 130, and change image generating section 140, described with reference to FIGS. 1 to 4.

The program mentioned above may be stored on an external recording medium. The recording medium is, for example, an optical recording medium such as DVD and PD, a magnet-optical recording medium such as MD, a tape medium, a semiconductor memory such as an IC card and the like, in addition to the flexible disk 1590 and CD-ROM 1595. The recording medium may be a storage device such as a hard disk and a RAM which is provided in a server system connected to a dedicated communication network or the Internet, and the program may be provided to the radiation image detecting system 100 via the network.

Although some aspects of the present invention have been described by way of an exemplary embodiment, it should be understood that those skilled in the art might make many changes and substitutions without departing from the spirit and the scope of the present invention which is defined only by the appended claims.

As is apparent from the above, an embodiment of the present invention can realize a radiation image detecting system, a radiation image detecting method, and a computer readable medium which make it possible to easily observe how blood is supplied to cells.

What is claimed is:

1. An image detecting system comprising:
an image detecting section configured for detecting a moving image of an examination subject into which a radiopaque contrast medium flows through one of an hepatic artery and a hepatic portal vein; and
a change image generating section configured for generating a change image representing a change in the moving image, the change being caused by movement of the radiopaque contrast medium after a timing at which the radiopaque contrast medium that has flown into one of the artery and the portal vein flows into capillaries;
wherein
the change image generating section is configured for generating (i) a change image when the radiopaque contrast medium flows into the examination subject through the artery and (ii) a change image when the radiopaque contrast medium flows into the examination subject through the portal vein, and
the image detecting system further comprises
an image processing apparatus that is configured to cause a display section to display the change images generated by the change image generating section, to emphasize a difference between (i) the change image when the radiopaque contrast medium flows into the examination subject through the artery and (ii) the change image when the radiopaque contrast medium flows into the examination subject through the portal vein by displaying a differential image between (i) the change image when the radiopaque contrast medium flows into the examination subject through the artery and (ii) the change image when the radiopaque contrast medium flows into the examination subject through the portal vein generated by the change image generating section.

2. The image detecting system as set forth in claim 1, further comprising
a timing identifying section configured for identifying the timing at which the radiopaque contrast medium that has flown into one of the artery and the portal vein flows into the capillaries, with reference to what is shown by the moving image.

3. The image detecting system as set forth in claim 2, wherein
the change image generating section is configured for generating the change image represented by a value obtained by integrating a pixel value of the moving image for a predetermined time period after the timing identified by the timing identifying section.

4. The image detecting system as set forth in claim 3, wherein
the change image generating section is configured for generating the change image represented by a value obtained by integrating, for the predetermined time period, a difference in pixel value between (i) the moving image detected after the timing identified by the timing identifying section and (ii) an image of the examination subject detected when the radiopaque contrast medium does not flow into the examination subject.

5. The image detecting system as set forth in claim 3, wherein
the change image generating section is configured for generating the change image represented by a value obtained by integrating, for the predetermined time period, a difference in pixel value between (i) the moving image detected after the timing identified by the timing identifying section and (ii) an image detected by the image detecting section at a timing near the timing identified by the timing identifying section.

6. The image detecting system as set forth in claim 2, further comprising
a pixel number calculating section configured for calculating the number of pixels whose pixel values fall within a predetermined range in each of images constituting the moving image, wherein
the timing identifying section is configured for identifying, as the timing at which the radiopaque contrast medium flows into the capillaries, a timing at which the number of pixels calculated by the pixel number calculating section becomes equal to or smaller than a predetermined number after taking a local maximal value.

7. The image detecting system as set forth in claim 2, wherein
the change image generating section is configured for generating the change image which is colored according to the change in the moving image which is caused after the timing identified by the timing identifying section.

8. The image detecting system as set forth in claim 1, wherein
the display section is configured to overlap (i) an image that is obtained by coloring, with a first color, the change image generated by the change image generating section when the radiopaque contrast medium flows into the examination subject through the artery and (ii) an image that is obtained by coloring, with a second color, the change image generated by the change image generating section when the radiopaque contrast medium flows into the examination subject through the portal vein, when displaying the images.

9. The image detecting system as set forth in claim 1, wherein
the image detecting section includes a radiation image detecting section configured for detecting a radiation moving image of the examination subject, the radiation moving image obtained after at least one of:
a step of injecting the radiopaque contrast medium through the artery, and
a step of injecting the radiopaque contrast medium through the portal vein said at least one injecting using a radiopaque contrast medium injector.

10. The system of claim 1 including a difference determination processor configured to determine the difference between (i) the change image when the radiopaque contrast medium flows into the examination subject through the artery and (ii) the change image when the radiopaque contrast medium flows into the examination subject through the portal vein for display by the display section.

11. The image detecting system as set forth in claim 1, wherein
the change image generating section adjusts luminance of at least one of (i) the change image when the radiopaque contrast medium flows into the examination subject through the artery and (ii) the change image when the radiopaque contrast medium flows into the examination subject through the portal vein such that the pixel values of a liver parenchyma are substantially the same luminance level, and then generates the differential image by calculating a difference between the resulting change images in which the luminance of at least one of the resulting change images (i) and (ii) was adjusted.

12. An image detecting method comprising:
  detecting a moving image of an examination subject into which a radiopaque contrast medium flows through one of an hepatic artery and a hepatic portal vein; and
  generating a change image representing a change in the moving image, the change being caused by movement of the radiopaque contrast medium after a timing at which the radiopaque contrast medium that has flown into one of the artery and the portal vein flows into capillaries;
  wherein
  the change image generating comprises generating (i) a change image when the radiopaque contrast medium flows into the examination subject through the artery and (ii) a change image when the radiopaque contrast medium flows into the examination subject through the portal vein, and
  the method further comprises
  displaying the change images generated by the change image generation to emphasize a difference between (i) the change image when the radiopaque contrast medium flows into the examination subject through the artery and (ii) the change image when the radiopaque contrast medium flows into the examination subject through the portal vein by displaying a differential image between (i) the change image when the radiopaque contrast medium flows into the examination subject through the artery and (ii) the change image when the radiopaque contrast medium flows into the examination subject through the portal vein generated by the change image generating section.

13. An image detecting method according to claim 12, wherein
  the change image generating step adjusts luminance of at least one of (i) the change image when the radiopaque contrast medium flows into the examination subject through the artery and (ii) the change image when the radiopaque contrast medium flows into the examination subject through the portal vein such that the pixel values of a liver parenchyma are substantially the same luminance level, and then generates the differential image by calculating a difference between the resulting change images (in which the luminance of at least one of the resulting change images (i) and (ii) was adjusted).

14. A non-transitory computer readable medium storing thereon a program for use with an image detecting system, when executed the program causing a computer to function as:
  an image detecting section configured for detecting a moving image of an examination subject into which a radiopaque contrast medium flows through one of an hepatic artery and a hepatic portal vein; and
  a change image generating section configured for generating a change image representing a change in the moving image, the change being caused by movement of the radiopaque contrast medium after a timing at which the radiopaque contrast medium that has flown into one of the artery and the portal vein flows into capillaries;
  wherein
  the change image generating section is configured for generating (i) a change image when the radiopaque contrast medium flows into the examination subject through the artery and (ii) a change image when the radiopaque contrast medium flows into the examination subject through the portal vein, and
  the image detecting system further comprises
  an image processing apparatus that is configured to cause a display section to display the change images generated by the change image generating section, to emphasize a difference between (i) the change image when the radiopaque contrast medium flows into the examination subject through the artery and (ii) the change image when the radiopaque contrast medium flows into the examination subject through the portal vein by displaying a differential image between (i) the change image when the radiopaque contrast medium flows into the examination subject through the artery and (ii) the change image when the radiopaque contrast medium flows into the examination subject through the portal vein generated by the change image generating section.

15. A non-transitory computer readable medium according to claim 14, wherein
  the change image generating section adjusts luminance of at least one of (i) the change image when the radiopaque contrast medium flows into the examination subject through the artery and (ii) the change image when the radiopaque contrast medium flows into the examination subject through the portal vein such that the pixel values of a liver parenchyma are substantially the same luminance level, and then generates the differential image by calculating a difference between the resulting change images in which the luminance of at least one of the resulting change images (i) and (ii) was adjusted.

16. An image detecting system comprising:
  an image detecting section configured for detecting a moving image of an examination subject into which a radiopaque contrast medium flows through one of an hepatic artery and a hepatic portal vein; and
  a change image generating section configured for generating a change image representing a change in the moving image, the change being caused by movement of the radiopaque contrast medium after a timing at which the radiopaque contrast medium that has flown into one of the artery and the portal vein flows into capillaries;
  a timing identifying section configured for identifying the timing at which the radiopaque contrast medium that has flown into one of the artery and the portal vein flows into the capillaries, with reference to what is shown by the moving image, and
  a pixel number calculating section configured for calculating the number of pixels whose pixel values fall within a predetermined range in each image constituting the moving image, wherein
  the timing identifying section is configured for automatically identifying, as the timing at which the radiopaque contrast medium flows into the capillaries, a timing at which the number of pixels calculated by the pixel number calculating section becomes equal to or smaller than a predetermined number after taking a local maximal value.

17. An image detecting system according to claim 16, wherein
  the change image generating section is configured for generating the change image represented by a value obtained by integrating a pixel value of the moving image for a predetermined time period after the timing identified by the timing identifying section.

* * * * *